US011627752B2

(12) United States Patent
Morel et al.

(10) Patent No.: US 11,627,752 B2
(45) Date of Patent: Apr. 18, 2023

(54) YEAST CELL WALL DERIVED FLAVOUR

(71) Applicant: DSM IP Assets B.V., Heerlen (NL)

(72) Inventors: Bernadette Theresia Morel, Echt (NL); Marco Alexander Van Den Berg, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 17/689,765

(22) Filed: Mar. 8, 2022

(65) Prior Publication Data
US 2022/0183332 A1  Jun. 16, 2022

Related U.S. Application Data

(62) Division of application No. 15/761,281, filed as application No. PCT/EP2016/071802 on Sep. 15, 2016, now Pat. No. 11,297,860.

(30) Foreign Application Priority Data

Sep. 21, 2015  (EP) ..................................... 15186044

(51) Int. Cl.
*A23L 27/21* (2016.01)
*A23L 9/10* (2016.01)
(Continued)

(52) U.S. Cl.
CPC .............. *A23L 27/21* (2016.08); *A23C 9/156* (2013.01); *A23L 2/56* (2013.01); *A23L 2/60* (2013.01); *A23L 9/12* (2016.08); *A23L 9/20* (2016.08); *A23L 23/00* (2016.08); *A23L 23/10* (2016.08); *A23L 27/23* (2016.08); *A23L 27/84* (2016.08); *A23L 31/15* (2016.08); *A23L 33/14* (2016.08); *C12Y 302/01* (2013.01); *C12Y 304/21* (2013.01); *C12Y 304/21062* (2013.01); *A23V 2002/00* (2013.01); *C12N 9/2405* (2013.01)

(58) Field of Classification Search
CPC ........ A23L 27/21; A23L 33/14; A23L 33/145; A23L 23/00; A23L 31/15; A23L 2/56; A23L 27/84; A23C 9/156
See application file for complete search history.

(56) References Cited

U.S. PATENT DOCUMENTS

2005/0058671 A1* 3/2005 Bedding .................... A61P 1/02
514/54
2006/0188625 A1 8/2006 Kortes
(Continued)

FOREIGN PATENT DOCUMENTS

WO  2013010937 A1  1/2013

OTHER PUBLICATIONS

PCT International Search Report for PCT/EP2016/071802, dated Nov. 24, 2016.
(Continued)

Primary Examiner — Changqing Li
(74) Attorney, Agent, or Firm — McBee Moore & Vanik IP, LLC; Susan McBee

(57) ABSTRACT

The present invention relates to a method for producing a flavour composition comprising providing a slurry of yeast cell walls and contacting the slurry of yeast cell walls with a glucanase and with an endoprotease, followed by separating a liquid fraction by solid/liquid separation to provide the liquid flavour composition.

17 Claims, 2 Drawing Sheets

(51) Int. Cl.
*A23C 9/156* (2006.01)
*A23L 2/56* (2006.01)
*A23L 9/20* (2016.01)
*A23L 33/14* (2016.01)
*A23L 23/00* (2016.01)
*A23L 23/10* (2016.01)
*A23L 27/00* (2016.01)
*A23L 31/15* (2016.01)
*A23L 27/23* (2016.01)
*A23L 2/60* (2006.01)
*C12N 9/24* (2006.01)

(56) References Cited

U.S. PATENT DOCUMENTS

| | | |
|---|---|---|
| 2006/0263415 A1 | 11/2006 | Sedmak |
| 2010/0143320 A1* | 6/2010 | Chossade .................. A61P 1/14 |
| | | 424/94.2 |
| 2010/0183767 A1 | 7/2010 | Noordam |
| 2012/0288587 A1 | 11/2012 | Cheng |
| 2014/0099402 A1 | 4/2014 | Noordam |

OTHER PUBLICATIONS

Conway, et al., "The effect of the addition of proteases and glucanases during yeast autolysison the production and properties of yeast extracts," Can. J. Microbiol., (2001), vol. 47: 18-24.

* cited by examiner

YEAST CELL WALL DERIVED FLAVOUR

CROSS-REFERENCE TO RELATED APPLICATIONS

This application is a division of U.S. application Ser. No. 15/761,281, filed 19 Mar. 2018, which is a National Stage entry of International Application No. PCT/EP2016/071802, filed 15 Sep. 2016, which claims priority to European Patent Application No. 15186044.2, filed 21 Sep. 2015. The content of each of these applications is incorporated by reference in its entirety.

BACKGROUND

Field of the Invention

The present invention relates to 5 a method for providing a flavour composition. According to another aspect the present invention relates to a flavour composition. According to yet another aspect the present invention relates to the use of a flavour composition.

Description of Related Art

Acceptability of food is highly influenced by its flavour (aroma and taste) perception, flavour release and mouthfeel. Mouthfeel is a term often used to refer to the tactile aspects of texture perception during consumption of food. For example, mouthfeel encompasses all of the "tactile (feel) properties perceived from the time at which solid, semi-solid or liquid foods or 15 beverages are placed in the mouth until they are swallowed." Following consumption, the mouth still senses residue and after effects resulting from the consumed food, such as astringency and mouth coating; after-feel is a term commonly used to describe these mechanical sensations that are also inherently part of texture perception.

For example fat is known to play an important role in providing a fatty and creamy 20 mouthfeel of food. However, the consumption of fat, or large amounts of fat, is undesired in view of health and overweight concerns. Therefore, there is an ongoing trend in reducing the fat content in food, such as in yogurts, milk, ice-cream, soups and sauces like mayonnaise etc.

Several research efforts have focused on ways to produce flavour compositions that provide similar functional and organoleptic properties such as fats but which are not readily 25 perceived as being synthetic. Examples of alternatives are carbohydrates and proteins which are common mouthfeel providers. However, a disadvantage of alternatives of fat is that they often sacrifice wholly or in part the fatty and creamy mouthfeel properties or impart less flavour and side notes, such as a milky note in case a creamer is used.

More recent research efforts focus on the modulation characteristics of flavour 30 compositions. Modulation of the flavour perception, flavour release and mouthfeel of food products by flavour compositions can be obtained by enhancement or masking of flavour notes of a food product the flavour composition is added to.

Yeast extracts are known for their taste enhancing properties. Yeast extracts comprise only the water soluble components of the yeast cell after removal of the yeast cell wall, the composition of which is primarily amino-acids, peptides, carbohydrates and salts. Yeast extract is produced through the hydrolysis of peptide bonds by the naturally occurring enzymes present in edible yeast 5 and/or or by the addition of food-grade enzymes (Food Chemical Codex), i.e. by autolysis and/or hydrolysis. Alternatively, yeast extracts could be obtained by mechanical or acid treatment of yeast cells. Yeast extracts are often used for providing savoury and umami flavour profiles. Yeast extracts are not known for enhancing a fatty and creamy mouthfeel without a savoury or an umami taste. Therefore, there is a need in 10 the art for flavour compositions which impart a fatty and creamy mouthfeel to food products.

SUMMARY

It was now surprisingly found that compositions derived from yeast cells walls by solubilisation of the cell walls provide modulation properties to a food product, and especially modulation characterised by an enhancement of a fatty and creamy mouthfeel or by taste masking. It was surprisingly found that yeast cell walls, which are normally discarded as 15 insoluble ingredients from the production of yeast extracts, can effectively be solubilised by enzymes and result in a flavour composition providing unique flavour profile modulating properties. Further, it was found that the flavour composition derived from the yeast cell walls provides fatty and creamy mouthfeel or enhancement of fatty and creamy mouthfeel, however without imparting the yeast characteristic savoury or umami flavour notes. Further it was found 20 that the present flavour composition is allows to reduce the fat content of a food product without compromising mouthfeel. Further it was found that the present flavour composition provides flavour modulation by masking.

DETAILED DESCRIPTION OF A PREFERRED EMBODIMENT

Definitions

Figure 1:
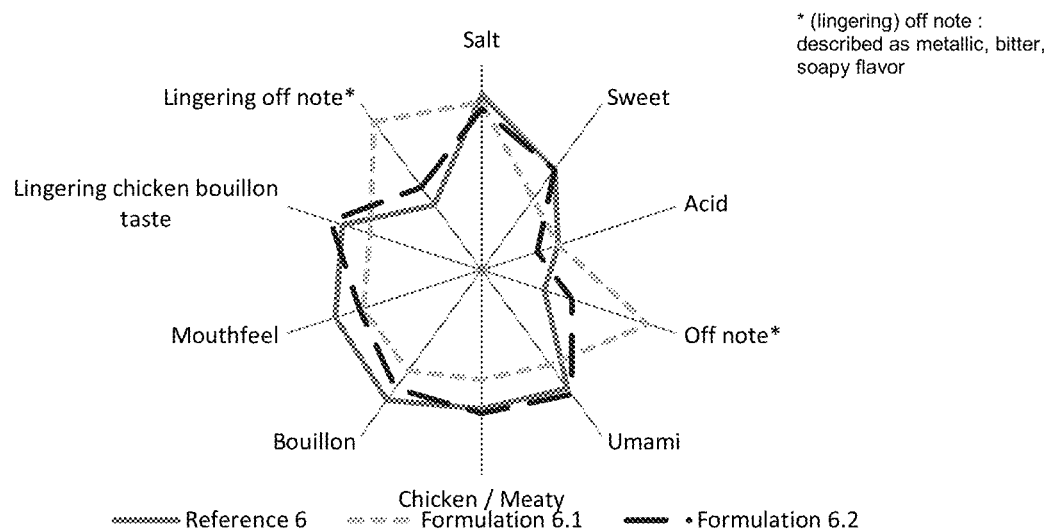
FIGS. 1-3 depict embodiments as described herein.

"Yeast cell walls" is defined herein insoluble cell walls from yeast cells derived as insoluble fraction after separation in a yeast autolysate or hydrolysate process. The insoluble cell walls represents 20-25% of the dry weight of the whole yeast cell. Preferably the yeast cells are from the genus *Saccharomyces*, more preferably *Saccharomyces cerevisiae*. The yeast may be produced in a fermentation process such as a process for the production of 30 common baker's yeast. Alternatively, the yeast cells are from the genus *Kluyveromyces, Candida* or Torula.

"A slurry of yeast cell walls" or "yeast cell wall slurry" is defined as a liquid or dried composition comprising insoluble yeast cells walls which composition comprises 15% to 35% (w/w) protein on dry weight and/or 5% to 20% (w/w) lipids on dry weight of the 35 composition. More preferably the yeast cell wall slurry comprises 15% to 40% (w/w) beta glucans and/or 10% to 30 (w/w) mannan-oligosaccharides on dry weight. Preferably the yeast cell wall slurry is a co-product of the production of yeast extracts.

"Protease" is defined herein as a hydrolase acting on peptide bonds in a protein substrate. An endoprotease acts on peptide bonds in an endo-fashion, i.e. cleaving the peptide bonds anywhere in the polypeptide chain in contrast to a (exo)peptidase which is defined herein as a hydrolase acting on peptide bonds in a protein substrate in an exo fashion, i.e. acting near the ends of the polypeptide chain. The endoproteases are divided into subclasses on the basis of their catalytic mechanism: serine endoproteases (EC 3.4.21.xx), cysteine endoproteases (EC 3.4.22.xx), aspartic endoproteases (EC 3.4.23.xx) and metallo-endoproteases (EC 3.4.24.xx).

A "proline-specific endoprotease" is defined herein as an endoprotease cleaving protein or oligopeptides substrates at the C-terminal side of a proline residue in the protein or oligopeptides substrate. The proline-specific endoprotease has been classified as EC 3.4.21.26. The enzyme can be obtained from various sources such as mammalian sources, bacteria (e.f. *Flavobacterium*) and fungi (*Aspergillus*, in particular *Aspergillus niger*). The enzyme of *Aspergillus niger* has been described in detail in WO02/45524, WO02/46381, WO03/104382. A suitable fungal enzyme from *Penicillium chrysogenum* is disclosed in WO2009/144269. A suitable bacterial enzyme from *Flavobacterium meningosepticum* is disclosed in WO03068170.

A "laminaripentaose producing β-1,3-glucanase", also known as LPHase, is a 3-1,3-glucanase that liberates laminaripentaose as the major product from polysaccharides such as laminarin, pachyman or curdlan. Laminaripentaose-producing-β-1,3-glucanase is a member of the glycoside hydrolase family 64 (abbreviated as GH-64). In JP6192589 (1986—Dainippon Ink & Chemicals), a laminaripentaose-producing-β-1,3-glucanase (or LPHase) of *Streptomyces matensis* DIC-108 is disclosed. The enzyme is used in a process to produce laminaripentaose from the polysaccharides curdlan, pachyman and/or laminarin.

A "flavour composition" is defined herein as a composition which can be safely used in food products for human consumption which composition improves the flavour (aroma and taste) perception, flavour release and/or mouthfeel of a food composition, by modulation of the flavour (aroma and taste) perception, flavour release and/or mouthfeel of a food composition. Modulating flavour perception, flavour release and/or mouthfeel of a food composition can be obtained by enhancing or masking of substances of a food composition.

DETAILED DESCRIPTION OF THE INVENTION

The present invention relates to a method for producing a flavour composition comprising providing a slurry of yeast cell walls and contacting the slurry of yeast cell walls with a glucanase and with an endoprotease, followed by separating a liquid fraction by solid/liquid separation to provide the flavour composition. Alternatively, the present invention relates to a method for producing a flavour composition comprising providing yeast cell walls and contacting the yeast cell walls with a glucanase and with an endoprotease, followed by separating a liquid fraction by solid/liquid separation to provide the flavour composition.

Preferably, the present flavour composition is a liquid flavour composition and/or the present flavour composition comprises the soluble fraction after contacting the yeast cell walls, or slurry of yeast cell walls, with a glucanase and/or endoprotease. Thus, preferably, the present step of separating a liquid fraction by solid/liquid separation provides the liquid flavour composition. The present inventors found that the process is able to efficiently solubilize the yeast cell walls in the slurry of yeast cell walls. Preferably, at least 60%, more preferably at least 70%, even more preferably at least 80% or even more than 90% of the yeast cell walls is solubilised to provide the flavour composition.

In a preferred embodiment, the present method further comprises contacting the slurry of yeast cell walls, or yeast cell walls, with an exopeptidase.

Preferably, contacting the yeast cell walls with a glucanase, endoprotease and/or with an exopeptidase is carried out simultaneously in view of the efficiency of the process. However, methods wherein the yeast cell walls are contacted with the glucanase, endoprotease and/or with an exopeptidase in any order are also envisaged.

The present glucanase, endoprotease and/or exopeptidase are yeast exogenous enzymes. The advantage of adding exogenous enzymes is a more controlled and efficient solubilisation of the yeast cell walls, providing high yields of solubilisation.

In a preferred embodiment, the present step of contacting the yeast cell walls with a glucanase, endoprotease and/or with an exopeptidase is carried out at a pH within the range of 3-10 and/or a temperature within the range of 40° C. to 70° C. More preferably, the present step of contacting the yeast cell walls with a glucanase, endoprotease and/or with an exopeptidase is carried out at a pH within the range of 4 to 8 or from 4 to 7, such as from 4.5 to 6.0 or from 5.0 to 6.0. More preferably, after controlling the initial pH, the pH during the present step of contacting the yeast cell walls with a glucanase, endoprotease and with an exopeptidase is not controlled. Preferably, the initial pH is within the range of 3 to 10, preferably from 4 to 8 or from 4 to 7, such as from 4.5 to 6.0 or from 5.0 to 6.0. Preferably, the temperature during the present step of contacting the yeast cell walls with a glucanase, endoprotease and/or with an exopeptidase is within the range of 40 to 70° C., such as from 45 to 65° C., or from 50 to 60° C.

Preferably, the yeast cell walls are contacted with a glucanase, endoprotease and/or with an exopeptidase for a time period within the range of 1 to 40 hours, such as from 2 to 30 hours or from 10 to 25 hours. The time period is dependent from the dosage of the glucanase, endoprotease and/or with an exopeptidase, and can be identified by the skilled person.

Preferably, the amount of glucanase during the step of contacting the yeast cell walls with glucanase is within the range of 0.01 to 5 wt % on dry matter yeast cell walls, more preferably within the range of 0.01 to 1 wt % or 0.05 to 1 wt % on dry matter yeast cell walls.

Preferably, the amount of endoprotease during the step of contacting the yeast cell walls with endoprotease is within the range of 0.01 to 10 wt % on dry matter yeast cell walls, more preferably within the range of 0.1 to 5 wt % on dry matter yeast cell walls.

Preferably, the amount of exopeptidase during the step of contacting the yeast cell walls with exopeptidase is within the range of 0.01 to 10 wt % on dry matter yeast cell walls, more preferably within the range of 0.1 to 5 wt % on dry matter yeast cell walls.

In a preferred embodiment, the endoprotease comprises a proline specific endoprotease. More preferably, the present endoprotease comprises a combination of an endoprotease with a proline specific endoprotease. Preferably, the amount of proline specific endoprotease during the step of contacting the yeast cell walls with proline specific endoprotease is within the range of 0.01 to 5 wt % on dry matter yeast cell walls, more preferably within the range of 0.1 to 2.5 wt % on dry matter yeast cell walls.

More preferably, the present proline-specific endoprotease is classified as EC 3.4.21.26. An example of a suitable proline specific endoprotease is disclosed in WO02/45524, WO02/46381, or in WO03/104382.

In a preferred embodiment, the present glucanase is a laminaripentaose-producing-β-1,3-glucanase or is LPHase. Laminaripentaose-producing-β-1,3-glucanase is efficiently used for degrading the glucans which are present in the yeast cell walls into smaller glucan fragments, such as laminaripentaoses. For example, degradation of the glucans into glucan fragments having a length of 1 to 50 kDa is found to efficiently solubilize the yeast cell walls. Preferably the present yeast cell walls comprise glucans comprising β-1,3-glucan and β-1,6-glucan bonds.

In a preferred embodiment, the present flavour composition comprises glucan fragments having a length of 0.1 or 0.5 to 50 kDa, preferably a length of 1 to 50 kDa, 2 to 50 kDa, 3 to 50 kDa, 4 to 50 kDa or 5 to 50 kDa. More preferably a length of 1 to 45 kDa, 1 to 40 kDa or 1 to 35 kDa. Even more preferably, the present glucan fragments have a length of 10 to 30 kDa.

In another preferred embodiment, the glucan fragments comprise β-1,3-glucan fragments and/or β-1,6-glucan fragments. Preferably the β-1,3-glucan fragments have a length of 5 to 20 kDa. Preferably, the β-1,6-glucan fragments have a length of 10 to 30 kDa.

In a preferred embodiment the present flavour composition is a fatty flavour composition. Accordingly, the present method may relate to a method for providing a fatty flavour composition. A fatty flavour composition is defined as a flavour composition which provides a fatty mouthfeel to a food product the flavour composition is added to.

In a preferred embodiment, the present method further comprises a step of contacting the slurry of yeast cell walls with a protease. More preferably the present step of contacting the slurry of yeast cell walls with a protease is at a temperature within the range of 40 to 80° C., such as from 50 to 70° C., or even from 55 to 65° C., and/or at a pH within the range of pH 6 to 10, such as from pH 7 to 9, or such as pH 8. The time period of contacting the slurry of yeast cell walls with a protease is preferably sufficient to hydrolyse the cell walls. Preferably the time period is within the range of 1 to 10 hours, such as from 2 to 8 hours. The dosage of the protease is preferably within the range of 0.01 to 10 wt % on dry matter yeast cell walls, more preferably within the range of 0.1 to 5 wt % on dry matter yeast cell walls. Preferably, the protease used for providing yeast cell walls is an endoprotease. It is preferred in the present method that the step of contacting the slurry of yeast cell walls with a protease is carried out before the present step of contacting the yeast cell walls with a glucanase and with an endoprotease.

The advantage of providing yeast cell walls by contacting yeast cell walls with a protease is that the proteins of the yeast cell walls, or fragments thereof, are solubilised, providing solubilisation of the yeast cell walls. Preferably, after providing yeast cell walls, the yeast cell walls are not separated from the solubilised matter before contacting the yeast cell walls with a glucanase and with an endoprotease.

Preferably, the present slurry of yeast cell walls, or yeast cell wall slurry, has a dry matter content of 5% to 25%. More preferably the slurry of yeast cell walls, or yeast cell wall slurry has a dry matter content of 10% to 20% such as from 12% to 18%.

In a preferred embodiment, the present method further comprises concentrating the flavour composition to a dry matter content of 5% to 60%, such as to a dry matter content of 10% to 50% or 30% to 40%. Concentration can be carried out by with an evaporator, such as with a falling film evaporator or a falling film plate evaporator.

In another preferred embodiment, the present method further comprises formulating the flavour composition with a spray dry carrier selected from salt, maltodextrin, yeast extract, starch, highly branched amylopectin, cellulose and gum Arabic, and/or spray drying the flavour composition to a dry matter content of at least 95%.

Given the advantageous flavour providing properties of the present flavour composition, the invention relates, according to another aspect, to a flavour composition, preferably a flavour composition derived from yeast cell walls, comprising glucans, mannans, amino acids, proteins or protein fragments and/or phospholipids. Preferably, the present flavour composition comprises:
- glucans and mannans;
- glucans and amino acids
- glucans and protein fragments
- phospholipids and glucans;
- phospholipids and mannans;
- phospholipids and amino acids;
- phospholipids and proteins or protein fragments;
- phospholipids, glucans and mannans;
- phospholipids, glucans and amino acids;
- phospholipids, glucans and proteins or protein fragments;
- phospholipids, glucans, mannans and amino acids;
- phospholipids, glucans, mannans and proteins;
- phospholipids, mannans and amino acids;
- phospholipids, mannans and proteins or protein fragments;
- phospholipids, glucans, mannans, amino acids and proteins or protein fragments. In a preferred embodiment, the amount of glucans in the present flavour composition is within the range of 0.5 to 50%, more preferably within the range of 1 to 40%, most preferably within the range of 10 to 35% (w/w, on carrier free dry matter).

In a preferred embodiment, the amount of mannans in the present flavour composition is within the range of 0.5 to 40%, more preferably within the range of 1 to 30%, most preferably within the range of 5 to 25% (w/w, on carrier free dry matter).

In a preferred embodiment, the amount of free amino acids in the present flavour composition is within the range of 0.5 to 30%, more preferably within the range of 1 to 25%, most preferably within the range of 5 to 15% (w/w, on carrier free dry matter).

In a preferred embodiment, the amount of protein or protein fragments in the present flavour composition is within the range of 0.5 to 40%, more preferably within the range of 1 to 40%, most preferably within the range of 5 to 35% (w/w, on carrier free dry matter).

In a further preferred embodiment, the amount of phospholipids in the present flavour composition is within the range of 0.5 to 40%, more preferably 1 to 35%, most preferably 5 to 25% (w/w, on carrier free dry matter).

In a further preferred embodiment, the present flavour composition comprises:
(i) 10 to 40% (w/w, on carrier free dry matter) glucans;
(ii) 5 to 30% (w/w, on carrier free dry matter) mannans;
(iii) 5 to 30% (w/w, on carrier free dry matter) free amino acids;
(iv) 10 to 40% (w/w, on carrier free dry matter) proteins or protein fragments; and/or
(v) 5 to 25%, (w/w, on carrier free dry matter) phospholipids.

Carrier free dry matter is defined as the dry matter of the flavour composition excluding a carrier. Carriers, known as drying aids, are generally used to make a process economically and technically viable and these additives should have a foodstuff status and contribute to increase the glass transition temperature of the mixture. Examples of such carriers are salt, maltodextrin, yeast extract, starch, highly branched amylopectin, cellulose and gum Arabic. The inventors of the present invention found that such a flavour composition is able to provide a fatty mouthfeel and allows to reduce fat content in a food product, without impairing the fatty mouth feel.

In a preferred embodiment, the present flavour composition comprises glucan fragments having a length of 0.5 to 50 kDa, preferably a length of 1 to 50 kDa, 2 to 50 kDa, 3 to 50 kDa, 4 to 50 kDa or 5 to 50 kDa. More preferably a length of 1 to 45 kDa, 1 to 40 kDa or 1 to 35 kDa. Even more preferably, the present glucan fragments have a length of 5 to 30 kDa.

In another preferred embodiment, the glucan fragments comprise β-1,3-glucan fragments and/or β-1,6-glucan fragments. Preferably the β-1,3-glucan fragments have a length of 5 to 20 kDa. Preferably, the β-1,6-glucan fragments have a length of 10 to 30 kDa.

The phospholipids are preferably selected from the group consisting of phosphatidic acids, phosphatidyl cholines, phosphatidyl ethanolamines, phosphatidyl serines, phosphatidyl glycerols, phosphatidyl inositols and mixtures thereof. Of these, phosphatidyl cholines, phosphatidyl glycerols and phosphatidic acids are particularly preferred.

In another preferred embodiment, the present flavour composition further comprises a carrier, preferably a spray dry carrier, selected from salt, maltodextrin, yeast extract, starch, highly branched amylopectin, cellulose and gum Arabic.

In a further preferred embodiment, the present flavour composition is in a spray dried form. The advantage of a spray dried form is ease of handling, dosing and storage.

According to another aspect, the present invention relates to the use of the present flavour composition for providing flavour modulation of a food product or for providing a modulated flavour profile of a food product.

Preferably, the present invention relates to the use of the present flavour composition for providing a fatty, creamy, mouthfeel and/or lingering flavour in a food product. Preferably the use of the present flavour composition for providing a fatty mouthfeel in a food product.

Preferably the present invention relates to the use of the present flavour composition for masking of bitter tastes or bitter flavours. More preferably the present invention relates to the use of the present flavour composition for bitter masking in low salt or in low sugar food products.

Alternatively, the present invention relates to the use of the present flavour composition for reducing the fat content in a food product or use in food having a reduced fat content. The inventors of the present invention found that the present flavour composition allows to reduce the fat content of a food product without impairing the fat perception of the food product.

Preferably the present food product is selected from the group consisting of soup, bouillon, sauces, gravy, mayonnaise, dressing, spreads, ready to eat meals, processed flavourings, processed meat, processed cheese, seasonings, noodles, butter, margarine, milk, yoghurt, ice creams, milkshakes and vegan or plant based dairy products. Preferable the food is selected from bouillon, skimmed milk, vanilla custard, chicken soup and ice tea.

In a further preferred embodiment, the present flavour composition is used in food products in an amount of at most 5% (w/w), preferably at most 2% (w/w), more preferably at most 1% (w/w), even more preferably at most 0.1% (w/w), most preferably at most 0.01% (w/w) of the food product. The flavour composition of the present invention is able to provide a desired flavour profile while it is dosed at small amounts. This is advantage in view of costs and in view of the texture of the food product, which is not disturbed by adding the present flavour composition in small amounts.

The invention will be further illustrated in the following non limiting examples. In the examples reference is made to the figures showing:

FIG. 1. Plot of the sensory evaluation of chicken bouillon formulations with 30% sodium reduction (n=7) in absence or presence of flavour composition from Example 1 (Ref 6=regular salt; Formulation 6.1=30% reduced salt; Formulations 6.2=30% reduced salt with flavour composition from Example 1).

Figure 2:
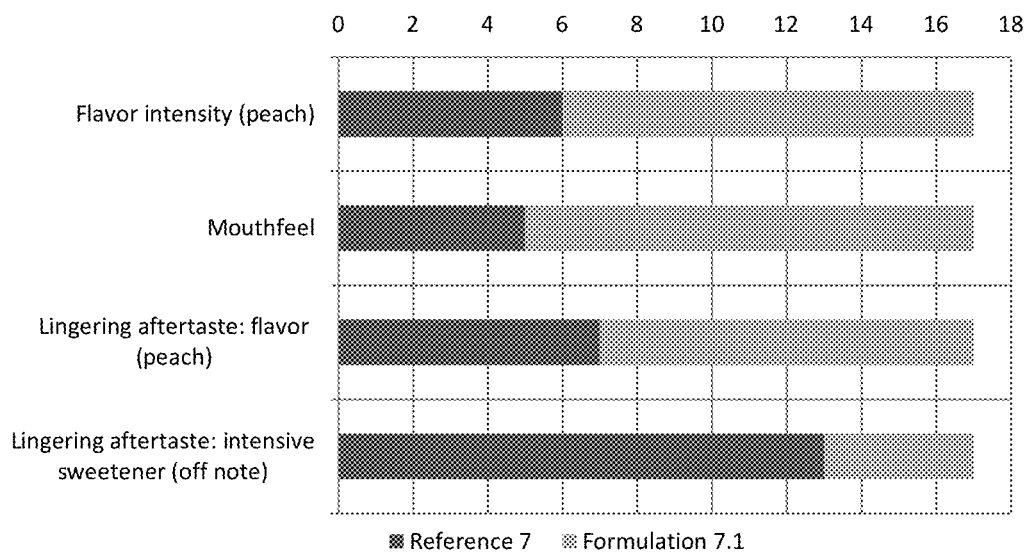

FIG. 2. Results of sensory evaluation Formulation 7.1 compared to reference 7, showing the amount of persons (n=17) indicating the highest intensity of the 4 selected attributes.

Figure 3:
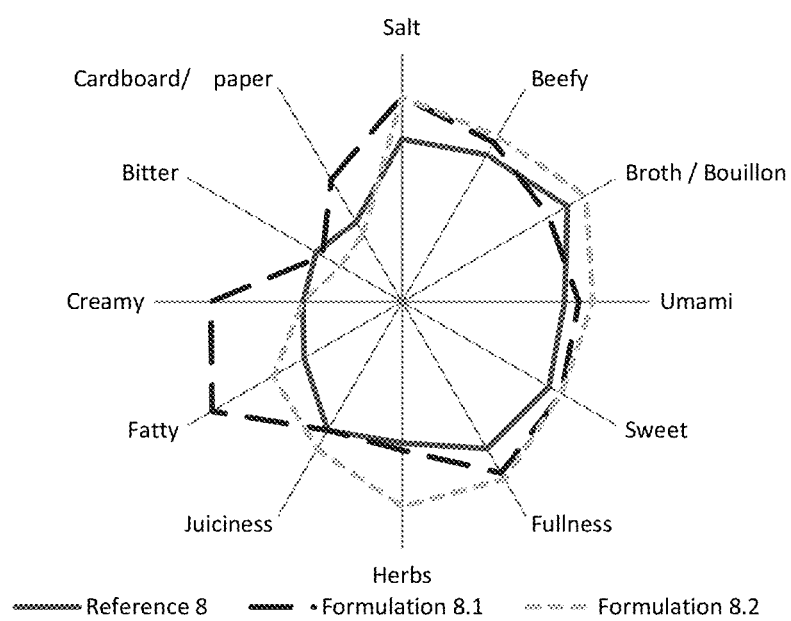

FIG. 3. Plot sensory evaluation fat free beef bouillon (n=6), comparing formulation 8.1 and formulation 8.2 to Reference 8. (Ref 8=fat free beef bouillon; Formulation 8.1=with flavour composition from Example 1; Formulations 8.2=with added Maxarome)

EXAMPLES

Example 1

Solubilisation of Yeast Cell Walls to Produce a Flavour Composition

Isolated yeast cell wall slurry with dry matter content of 12-15% dry matter, was incubated at a concentration of 1.0% wt % dm for 4 h at 60° C. with Alcalase (Novozymes, Bogsvaerd, Denmark, endoprotease). The pH was controlled at pH 8. At the end of this incubation the pH of the yeast cell wall slurry was adjusted to 5.3.

Subsequently, the slurry was incubated with Denazyme GEL-L1 (Nagase Biochemicals, Kyoto, Japan, β-(1,3) glucanase) at 0.07 wt % dm and the proteases: Flavourzyme (Novozymes, Bogsvaerd, Denmark, endoprotease and exopeptidase) at a dose of 0.5 wt % dm and proline-specific endoprotease (as disclosed in WO02/45524) at a dose of 0.5 wt %. The yeast cell walls were hydrolysed during 16 hours at 55° C.

After this incubation the enzymes were heat inactivated. The residual insoluble dry matter was removed by centrifugation. The solubilized cell wall material was concentrated by falling fill evaporator to a concentrate with a dry matter content of 30-35% dm. Different carriers were chosen to spray dry the Flavour composition. A high salt (HS) Flavour composition was produced after addition of 40% salt on total dry matter. A low salt (LS) Flavour composition was formulated by addition of 20% maltodextrin on total dry matter. The content of the provided flavour composition is shown in table 1.

TABLE 1 content flavour composition

| Component | % on carrier free dry matter |
| --- | --- |
| Glucan fragments | 27 |
| Mannans | 18 |
| Free amino acids | 13 |

TABLE 1-continued

| content flavour composition | |
|---|---|
| Component | % on carrier free dry matter |
| Protein/protein fragments | 31 |
| Phospholipids | 11 |

Example 2

Increase of Fatty Mouthfeel of Fat Free Chicken Bouillon

A fat free chicken bouillon was prepared by dry blending all ingredients from Table 2 in tap water of 95° C. and stirred until homogeneity. Products were cooled down until 60° C. before sensorial evaluation.

TABLE 2

Compositions of formulations; all numbers in weight (gr)

| Ingredients | Formulation 1.1 | Reference 1 |
|---|---|---|
| Flavour composition from example 1 | 0.5 | 0 |
| Sodium chloride | 6.8 | 7.0 |
| Monosodium glutamate | 1.6 | 1.6 |
| Onion powder | 0.25 | 0.25 |
| Turmeric | 0.06 | 0.06 |
| White pepper | 0.04 | 0.04 |
| Celery leaves dried | 0.04 | 0.04 |
| Disodium Guanosine-5'-monophosphate (GMP) | 0.06 | 0.06 |
| Disodium Inosine-5'-monophosphate (IMP) | 0.06 | 0.06 |
| Maltodextrin | 10.25 | 10.55 |
| Maxavor Key Chicken YEX | 0.3 | 0.3 |
| Boiled Chicken Flavour | 0.04 | 0.04 |
| Water | 1000 | 1000 |

The samples were evaluated by a trained sensory panel for savoury applications (n>10) by means of a paired comparison test (replicate measurement). A basic chicken application (Reference 1) and the basic application with added Flavour composition from Example 1 (Formulation 1.1) were offered simultaneously to the panelists with the question to identify the sample with the highest fatty mouthfeel character. Between and within the comparisons, the samples were offered randomly to the panelists. Based on the chance level of the test method a proportion of 0.5 is expected if no difference can be detected between two samples.

TABLE 3

| Sample | Correct proportion |
|---|---|
| Formulation 1.1 | 0.78 |
| Reference 1 | 0.53 |

Table 3 indicates the proportion of panelists that selected the sample with added Flavour composition from Example 1 (Formulation 1.1) having the most fatty mouthfeel character is 0.78. A significant effect on fatty mouthfeel character was found after addition of 0.05% Flavour composition from Example 1 to the basic chicken application (Reference 1).

Example 3

Mouthfeel Enhancement in Chicken Bouillon

After dry blending of all ingredients of Reference 2, Formulation 2.1 and Formulation 2.2 (Table 4) to prepare chicken bouillon and chicken bouillon containing flavour composition from Example 1 at two different dose levels, the ingredients were added in tap water of 95° C. and stirred until homogeneity. Products were cooled down until 60° C. before sensorial evaluation.

TABLE 4

Compositions of formulations; all numbers in weight (gr)

| Ingredients | Formulation 2.1 | Formulation 2.2 | Reference 2 |
|---|---|---|---|
| Flavour composition from example 1 | 0.5 | 1.5 | 0 |
| Vegetable fat | 5.0 | 5.0 | 10.0 |
| Sodium chloride | 6.8 | 6.4 | 7.0 |
| Maltodextrin | 5.25 | 4.65 | 0.55 |
| Monosodium glutamate | 1.6 | 1.6 | 1.6 |
| Onion powder | 0.25 | 0.25 | 0.25 |
| Turmeric | 0.06 | 0.06 | 0.06 |
| White pepper | 0.04 | 0.04 | 0.04 |
| Celery leaves dried | 0.04 | 0.04 | 0.04 |
| Disodium Guanosine-5'-monophosphate (GMP) | 0.06 | 0.06 | 0.06 |
| Disodium Inosine-5'-monophosphate (IMP) | 0.06 | 0.06 | 0.06 |
| Maxavor Key Chicken YEX | 0.3 | 0.3 | 0.3 |
| Boiled Chicken Flavour | 0.04 | 0.04 | 0.04 |
| Water | 1000 | 1000 | 1000 |

The samples were evaluated by a trained sensory panel for savoury applications (n=4). A basic chicken bouillon (Reference 2) and the basic chicken bouillon with added flavour composition from Example 1 at two different dose levels (Formulation 2.1 and Formulation 2.2) were offered in one single set to the expert panelists and the panelists were asked to describe the product character, focused on attributes relevant for mouthfeel enhancement like fatty, creamy and fat coating.

TABLE 5

Descriptive evaluation results of the expert panel comparing Formulation 2.1 and Formulation 2.2 with Reference 2.

| Sample | Descriptive evaluation result |
|---|---|
| Formulation 2.1 | A creamy taste. Smooth, creamy, soft, velvet like taste. Small fat particle size. |
| Formulation 2.2 | An even more creamy taste than Formulation 2.1. Smooth, creamy, soft, velvet like taste. Small fat particle size. |
| Reference 2 | Fatty, peaky flavour profile. Fat coating. Large oil droplets were visible. |

Table 5 discloses that the formulation with added flavour composition according to the invention provides a creamy taste while the amount of vegetable fat is reduced with 50%.

Example 4

Enhancement of Fatty and Creamy Mouthfeel in Semi Skimmed Milk

In a semi skimmed milk from a commercial supplier, the flavour composition from Example 1 was added (Formulation 3.1) to investigate its mouthfeel enhancing properties. After addition the milk was gently stirred until homogeneity.

TABLE 6

Compositions of formulations; all numbers in weight (gr)

| Ingredients | Formulation 3.1 | Reference 3 |
|---|---|---|
| Flavour composition from example 1 | 1.0 | 0 |
| Semi skimmed milk (pasteurized) | 1000 | 1000 |

The samples (Table 6) were evaluated by a trained sensory panel (n=6). The semi skimmed milk from a commercial supplier (Reference 3) and the semi skimmed milk from a commercial supplier with added flavour composition from Example 1 (Formulation 3.1) were offered in one single set to the expert panelists and the panelists were asked to describe the product character, focused on attributes relevant for mouthfeel enhancement like fatty, creamy and fat coating.

TABLE 7

Descriptive evaluation results of the expert panel comparing Formulation 3.1 with Reference

| Sample | Descriptive evaluation result |
|---|---|
| Formulation 3.1 | More mouthfeel (more creamy and fatty) than the comparative sample Reference 3, somewhat more sweet. Also a slight cooked flavour. |
| Reference 3 | Fresh, neutral, milk |

The expert panelist indicated that Formulation 3.1 that contained the flavour composition from Example 1, clearly showed an increased fatty, creamy mouthfeel compared to the commercial semi skimmed milk (Table 7). Thus, the flavour composition of the present invention modulates the sensory impact of the milk by increasing the fatty, creamy mouthfeel.

Example 5

Improve Flavour Balance and Creamy Mouthfeel in Vanilla Custard

To prepare a vanilla custard, all ingredients were weighted (Table 8). Reference 4.1 was prepared with semi skimmed milk from a commercial supplier, and Reference 4.2 was prepared with full fat milk from a commercial supplier. The flavour composition from Example 1 was added (Formulation 4.1) to investigate its mouthfeel enhancing properties in comparison to the vanilla custard prepared with semi skimmed milk (Reference 4.1) and the vanilla custard prepared with full fat milk (Reference 4.2).

TABLE 8

Compositions of formulations; all numbers in weight (gr)

| Ingredients | Formulation 4.1 | Reference 4.1 | Reference 4.2 |
|---|---|---|---|
| Flavour composition from example 1 | 0.4 | 0 | 0 |
| Semi skimmed milk | 749.30 | 749.30 | 0 |
| Full fat milk | 0 | 0 | 749.3 |

TABLE 8-continued

Compositions of formulations; all numbers in weight (gr)

| Ingredients | Formulation 4.1 | Reference 4.1 | Reference 4.2 |
|---|---|---|---|
| Egg yolk | 85.60 | 85.60 | 85.60 |
| Sugar | 139.1 | 139.1 | 139.1 |
| Starch | 17.1 | 17.1 | 17.1 |
| Vanilla | 5.40 | 5.40 | 5.40 |
| Carrageenan | 2.10 | 2.10 | 2.10 |
| Xanthan gum | 1.30 | 1.30 | 1.30 |
| Colouring | 0.016 | 0.016 | 0.016 |

All ingredients were mixed together and then heated until cooking and kept at cooking conditions for approximately 5 minutes. The formulations were homogenized using a high shear mixer to obtain a smooth structure. All formulations were cooled overnight at refrigerator temperature.

One hour before sensorial evaluation, the formulations were relocated from the refrigerator to ambient temperature. The samples were evaluated by an expert panel (n=9). The vanilla custard produced with semi skimmed milk (Reference 4.1), the vanilla custard produced with full fat milk (Reference 4.2) and the vanilla custard produced with semi skimmed milk with added flavour composition from Example 1 (Formulation 4.1) were offered in one single set to the expert panelists and the panelists were asked to describe the product character, focused on attributes relevant for mouthfeel enhancement like fatty, creamy and fat coating.

TABLE 9

Descriptive evaluation results of the expert panel comparing Formulation 4.1 with Reference 4.1 and Reference 4.2.

| Sample | Descriptive evaluation result |
|---|---|
| Formulation 4.1 | The sweetness impact and release is changed. The initial sweetness is slightly lower than Reference 4.1 and the whole profile becomes more balanced. The creaminess and fattiness is enhanced. Three panelists indicated that this product showed comparable fattiness to the custard prepared with full fat milk (Reference 4.2). |
| Reference 4.1 | Initial sweet and vanilla impact. Low on creaminess and no fattiness. Product not very balanced. |
| Reference 4.2 | Much lower on sweetness and vanilla taste. But the whole profile seems balanced and very creamy and fatty. |

The expert panelists indicated that Formulation 4.1 that contained the flavour composition from Example 1, showed an enhanced creaminess and fattiness compared to vanilla custard of Reference 4.1 (Table 9). In addition three panelists indicated that the fattiness of Formulation 4.1 containing the flavour composition from Example 1, was comparable to the fattiness of the vanilla custard produced with full fat milk (Reference 4.2) confirming the mouthfeel enhancement as a result of the addition of the flavour composition from Example 1 as well as showing the capability of the present flavour composition to reduce the fat content in a food product.

Example 6

Bitter Masking in Low Salt Chicken Soup

A fat free chicken bouillon was prepared by dry blending all ingredients from Table 10 in tap water of 95° C. and stirred until homogeneity. Products were cooled down until 60° C. before sensorial evaluation.

TABLE 10

Compositions of formulations; all numbers in weight (gr)

| Ingredients | Formulation 6.1 | Formulation 6.2 | Reference 6 |
|---|---|---|---|
| Flavour composition from example 1 | | 0.5 | |
| Maltodextrin | 10.3 | 10 | 10.51 |
| Sodium chloride | 4.9 | 4.7 | 7.0 |
| Potassium chloride | 2.31 | 2.31 | 0.0 |
| Monosodium glutamate | 1.6 | 1.6 | 1.6 |
| Maxavor Key Chicken YEX | 0.3 | 0.3 | 0.3 |
| Onion powder | 0.25 | 0.25 | 0.25 |
| Disodium Guanosine-5'-monophosphate (GMP) | 0.06 | 0.06 | 0.06 |
| Disodium Inosine-5'-monophosphate (IMP) | 0.06 | 0.06 | 0.06 |
| Turmeric | 0.06 | 0.06 | 0.06 |
| White pepper | 0.04 | 0.04 | 0.04 |
| Celery leaves dried | 0.04 | 0.04 | 0.04 |
| Chicken Boiled Flavour | 0.08 | 0.08 | 0.08 |
| Water | 1000 | 1000 | 1000 |

The samples were evaluated by a trained sensory panel for savoury applications (n=7). A basic chicken bouillon (Reference 6) and the basic chicken bouillon reduced in salt by 30% (with added potassium chloride to repair the salty taste) without and with added flavour composition from Example 1 (Formulation 6.1 and Formulation 6.2) were offered in one single set to the expert panelists, in random order and blindly coded. Before conducting the test, first the panelists were asked to determine the main attributes which they find suitable for this application. And a bouillon with 0% and 4% potassium chloride was tasted to make sure all experts recognize the taste and score it within the off note attribute. For the test the experts had to score the products on a 5 point scale, of which the outcome is presented in FIG. 1.

The expert panelists indicated that Formulation 6.2 that contained the flavour composition from Example 1, clearly showed a masking effect of the salt reduced formulation using KCl (Formulation 6.1). Addition of the flavour composition from Example 1 restored the balance, and it lowered the off note which was present due to the addition of KCl.

Example 7

Bitter Masking and Improve Mouthfeel in Sugar Free Ice Tea

Intensive sweeteners are effectively used to replace sugar in beverage systems, however the final product can suffer of a loss in mouthfeel (body), increase of lingering off notes in the aftertaste (which is often perceived as a type of bitterness). The flavour composition from Example 1 was added to a sugar free ice tea from a commercial supplier (Bolero Drinks Ltd) (Formulation 7.1) to investigate its mouthfeel enhancing properties and masking properties. The powdered ice tea was prepared, according to the instructions of the supplier, and the flavour composition from Example 1 was gently stirred in until homogeneity.

TABLE 11

Compositions of formulations; all numbers in weight (gr)

| Ingredients | Formulation 7.1 | Reference 7 |
|---|---|---|
| Flavour composition from example 1 | 0.3 | 0 |
| Ice Tea Peach (Instant peach flavoured drink with black tea extract and sweeteners) | 8 | 8 |
| Water | 1500 | 1500 |

The samples (Table 11) were evaluated by a group of people (n=17). The Ice Tea Peach from a commercial supplier (Reference 7) and the Ice Tea Peach from a commercial supplier with added flavour composition from Example 1 (Formulation 7.1) were offered simultaneously to each person. Each person had to indicate which sample had the highest intensity, on four different attributes.

FIG. 2 shows the amount of persons that selected either Reference 7 or the sample with added Flavour composition from Example 1 (Formulation 7.1) having the highest intensity for each attribute.

The overall result of the sensory group shows that the mouthfeel of the ice tea was increased and the lingering off notes (due to the use of artificial sweeteners) were decreased when the flavour composition from Example 1 was added (Formulation 7.1).

Example 8

Sensory Evaluation Maxarome Versus Flavour Composition from Example 1

A fat free beef bouillon was prepared by dry blending all ingredients from Table 12 in tap water of 95° C. and stirred until homogeneity. Products were cooled down until 60° C. before sensorial evaluation.

TABLE 12

Compositions of formulations; all numbers in weight (gr)

| Ingredients | Formulation 8.1 | Formulation 8.2 | Reference 8 |
|---|---|---|---|
| Flavour composition from example 1 | 2.4 | 0 | 0.00 |
| Maxarome YE (DSM Food specialties BV) | 0 | 2.4 | 0 |
| Sodium chloride | 4.24 | 4.24 | 5.20 |
| Maltodextrin | 7.40 | 7.40 | 8.84 |
| Maxavor Roast Beef YE (DSM Food specialties BV) | 2.00 | 2.00 | 2.00 |
| Modified starch | 1.7 | 1.7 | 1.7 |
| Beef extract | 0.8 | 0.8 | 0.8 |
| Sugar | 0.70 | 0.70 | 0.70 |
| Onion powder | 0.40 | 0.40 | 0.40 |
| Caramel powder | 0.18 | 0.18 | 0.18 |
| Garlic powder | 0.06 | 0.06 | 0.06 |
| White pepper | 0.04 | 0.04 | 0.04 |
| Citric acid | 0.030 | 0.030 | 0.030 |
| Tumeric | 0.030 | 0.030 | 0.030 |
| Nutmeg | 0.02 | 0.02 | 0.02 |
| Laurel | 0.01 | 0.01 | 0.01 |
| Water | 1000 | 1000 | 1000 |

The three samples were evaluated by a trained sensory panel for savoury applications (n=6). A basic beef bouillon (Reference 8), a basic beef bouillon with added Maxarome (Formulation 8.2), and a basic beef bouillon with added flavour composition from Example 1 (Formulation 8.1) were offered in one single set to the expert panelists in random order and blindly coded. For the test the experts had to score the products at the selected attributes on a 5 point scale, of which the outcome is presented in FIG. 3.

The expert panelists indicated that Formulation 8.1 that contained the flavour composition from Example 1, clearly showed an increase in fatty and creamy notes, compared to the reference. While Formulation 8.2 containing Maxarome, only resulted in a minor increase in fattiness compared to the reference, and primarily enhanced on bouillon, umami and herbs.

The invention claimed is:

1. A flavour composition, wherein the flavour composition comprises at least one of solubilized glucans, mannans, amino acids, proteins, protein fragments, and phospholipids, wherein the flavour composition consists of the soluble fraction derived from isolated and solubilized yeast cell walls.

2. The flavour composition according to claim 1, comprising:
    (i) 10 to 40% (w/w) solubilized glucans having a length of 0.1 to 50 kD;
    (ii) 5 to 30% (w/w) mannans;
    (iii) 5 to 30% (w/w) free amino acids;
    (iv) 10 to 40% (w/w) protein; and
    (v) 5 to 25% (w/w) phospholipids.

3. The flavour composition according to claim 2, wherein the flavour composition is in spray-dried form.

4. A food product comprising the flavour composition according to claim 2.

5. The food product according to claim 4, which is a reduced-fat or fat-free product.

6. The food product according to claim 4, which is a reduced-salt food product.

7. The food product according to claim 4, which is selected from the group consisting of soup, bouillon, sauce, gravy, mayonnaise, dressing, spread, processed flavouring, processed meat, processed cheese, seasonings, noodles, butter, margarine, milk, skimmed milk, yoghurt, ice cream, milkshake, custard, ice tea, vegan dairy products, and plant-based dairy products.

8. The food product of claim 7, which is selected from the group consisting of bouillon, skimmed milk, vanilla custard, chicken soup, and ice tea.

9. A food product comprising the spray-dried flavour composition according to claim 3.

10. The flavour composition according to claim 2, which is concentrated to a dry matter content of 30 to 40%.

11. The food product according to claim 4, which comprises the flavour composition in an amount of at most 5% w/w.

12. The food product according to claim 11, which comprises the flavour composition in an amount of 0.01% to 1%.

13. The food product according to claim 12, which comprises the flavour composition in an amount of 0.05%.

14. The spray-dried flavor composition according to claim 3 comprising:
    10 to 40% (w/w) solubilized glucans having a length of 0.1 to 50 kD;
    (ii) 5 to 30% (w/w) mannans;
    (iii) 5 to 30% (w/w) free amino acids;
    (iv) 10 to 40% (w/w) protein; and
    (v) 5 to 25% (w/w) phospholipids,
    and a carrier selected from the group consisting of salt, maltodextrin, yeast extract, starch, highly branched amylopectin, cellulose, and gum Arabic.

15. The spray-dried flavour composition according to claim 14, wherein the spray-dried composition comprises a dry matter content of at least 95% w/w.

16. The flavour composition according to claim 1, which is a liquid.

17. The flavour composition according to claim 2, which is a liquid.

* * * * *